(12) United States Patent
Gipp et al.

(10) Patent No.: US 7,871,821 B2
(45) Date of Patent: Jan. 18, 2011

(54) ARTIFICIAL TESTING SOIL AND METHOD OF TESTING

(75) Inventors: Mark M. Gipp, Racine, WI (US); John R. Wietfeldt, Franksville, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 987 days.

(21) Appl. No.: 11/323,931

(22) Filed: Dec. 30, 2005

(65) Prior Publication Data

US 2006/0160225 A1    Jul. 20, 2006

Related U.S. Application Data

(63) Continuation-in-part of application No. 10/172,637, filed on Jun. 14, 2002, now Pat. No. 7,001,773.

(60) Provisional application No. 60/298,645, filed on Jun. 15, 2001.

(51) Int. Cl.
*G01N 33/00* (2006.01)
*G01N 1/00* (2006.01)

(52) U.S. Cl. .............................. 436/8; 436/19; 436/183; 252/408.1; 252/88.1; 252/88.2

(58) Field of Classification Search .................. 436/8, 436/19, 183; 252/88.1, 88.2, 408.1
See application file for complete search history.

(56) References Cited

U.S. PATENT DOCUMENTS

| | | | |
|---|---|---|---|
| 4,792,363 A | 12/1988 | Franklin et al. | |
| 5,090,975 A | 2/1992 | Requejo | |
| 5,461,749 A | 10/1995 | Ahlberg | |
| 5,802,667 A * | 9/1998 | Williams | 15/395 |
| 5,877,138 A | 3/1999 | Ditze | |
| 6,302,936 B1 * | 10/2001 | Adam | 71/13 |
| 6,419,722 B1 | 7/2002 | Adam | |
| 6,846,858 B2 | 1/2005 | Lemay | |
| 2002/0050016 A1 | 5/2002 | Willman | |
| 2003/0008402 A1 | 1/2003 | Lepow | |
| 2006/0160225 A1 | 7/2006 | Gipp et al. | |

FOREIGN PATENT DOCUMENTS

| | | | |
|---|---|---|---|
| EP | 0477007 A | | 3/1992 |
| GB | EP0477007 | * | 9/1991 |
| WO | WO 0110970 A1 | | 2/2001 |
| WO | WO 02102918 A1 | | 12/2002 |

OTHER PUBLICATIONS

International Search Report and Written Opinion dated Jul. 17, 2007 for PCT/US2006/049026.

* cited by examiner

*Primary Examiner*—Krishnan S Menon
*Assistant Examiner*—Rebecca Fritchman

(57) ABSTRACT

An artificial test soil comprises particulate, hair, and fiber components, wherein said particulate component consists of mineral, food, and plant materials, so chosen and proportioned as to correlate to a typical soil found in the home. The test soil may be used to test cleaning products by application of a known amount thereof to a surface, cleaning of said surface, and determination of the amount of said soil removed from said surface.

11 Claims, No Drawings

ARTIFICIAL TESTING SOIL AND METHOD OF TESTING

CROSS-REFERENCE TO RELATED APPLICATIONS

This application is a continuation-in-part of U.S. patent application Ser. No. 10/172,637, filed on Jun. 14, 2002, now U.S. Pat. No. 7,001,773 which claims the benefit of U.S. Provisional Application Ser. No. 60/298,645, filed Jun. 15, 2001.

BACKGROUND OF THE INVENTION

This invention relates to a synthetic soil composition for use in testing cleaning implements with or without separate or combined cleaning compositions, and a method of conducting such testing. Dusting devices and cleaning cloths need to pick up dust and dirt commonly found around the home. There is a need to be able to consistently test these cloths and cleaning devices to allow comparisons that will accurately correlate to how these cloths and devices will perform in the "real world". Since there can be a wide variation of dust and dirt found in a typical home environment, and even the same home over differing periods of time, it is not considered feasible to collect soil, from an individual home, or even a series of homes, and use this as a reproducible testing material.

In the past, various artificial soils and test methods have been attempted for this purpose, but none have been found to correlate to what could be considered a typical home environment. For example, U.S. Pat. No. 5,928,948, of Malchesky, teaches a method for assessment and evaluation of a cleaning process comprising the steps of contaminating a porous material with a known soil, subjecting the porous material and the soil to the cleaning process to be assessed and evaluated, and evaluating the cleaning process on the basis of the soil not removed by the cleaning process. The test procedure of the present invention does not involve contamination of a porous material, and the soil employed by the patentee does not correspond to the soil of the present invention, but is more closely related to organic contamination more likely found in a medical, dental, surgical, or veterinary facility than in a typical home environment.

In U.S. Pat. No. 4,867,614, Freed teaches a composite mixture comprising soil and from about 0.1 to 5 percent of additive discrete fiber materials. The soil comprises natural soil selected from a group including sand, clay, and mixtures thereof, and the fiber materials are discrete fibers selected from man-made fiber forming substances and fiberglass, present to improve the punching resistance, total angle of internal friction, average total cohesion, and average initial tangent modulus of the soil. The present test soil is not reinforced so as to provide improved engineering properties as is that of the patentee. The composite soil mixture of the patent is provided to have improved load bearing capability and related engineering properties to benefit foundations and column supports, while the present invention is designed to correspond to a typical form of dirt or soil to be found in a typical home setting and the two soils have little in common.

U.S. Pat. Nos. 6,302,936 and 6,419,722, of Adam, claims an artificial soil composition comprising a homogenous mixture of a blending base, cellulose, bio-solids, calcium in any form burned crop waste or vegetation, and ammonium sulfate. Also claimed is a process for making the artificial soil. The purpose of the artificial soil proposed by Adam is for crop growth, rather than for a test material for evaluation of a cleaning composition or method, and the artificial soil of Adam comprises a very different mixture than that of the present invention.

In U.S. Pat. No. 5,312,661, Suzuki et al. teaches an artificial soil comprising porous granules consisting essentially of a plurality of thermoplastic resin foamed particles. The present invention does not include the presence of thermoplastic resin foamed particles, which are present in the patented composition to provide improved air permeability and drainage, which properties would not be of value in the purpose of the present invention.

A synthetic test soil is taught by Pfeifer, in U.S. Pat. No. 6,107,097, relating to test stains comprising isolated fibrin and/or fibrin precursors and blood plasma proteins. The present invention does not comprise fibrins or fibrin precursors, and does not relate to the testing of cleaning procedures for medical or surgical instruments.

In addition to the above, the following patents further show the state of the art: U.S. Pat. No. 5,137,460, of Middleton; U.S. Pat. No. 5,397,392, of Derr; U.S. Pat. No. 5,502,998, of Miller et al.; U.S. Pat. No. 5,583,165, of Kviesitis; Franklin et al. U.S. Pat. No. 4,792,363; Requejo et al., U.S. Pat. No. 5,090,975; Ahlberg et al., U.S. Pat. No. 5,461,749; Ditze et al., U.S. Pat. No. 5,877,138; Willman et al., U.S. Patent Application Publication No. US 2002/0050016; Lemay, U.S. Pat. No. 6,846,858; and Japanese Patent 7-35680, of Noritake et al. However, none of the prior art shows a soil which is typical of the type of soil or dirt to be found in a normal home or non-medical work environment, or a method for testing a cleaning composition, implement, or procedure suitable for use in such a normal home environment. It is also to be noted that the present invention is intended to be used in a hard surface cleaning environment, as opposed to a carpeted environment. Thus, the test soil of the present invention is intended to correlate to a soil or dust normally found on hard surface areas of the home, not in a carpeted area, and accordingly, the artificial test soil of the invention is not anticipated to be similar to soil removed from carpeting by vacuum cleaning.

Furthermore, these prior soil compositions relate generally to compositions which are normally found on a floor surface of a home, such as a carpeted, hardwood, tile, or other flooring surface. Thus, these test soils do not accurately reflect the types of fibers and particulates which form dust compositions that, in addition to being found on flooring surfaces, are also located on other surfaces elevated above the flooring surface, such as on tables, chairs, and window sills, among others. The reason for this is that the dust composition is formed of lighter components than typical soil compositions that enable the dust compositions to be carried in vertical as well as horizontal directions by air currents in the home. Thus, because of this difference in composition from normal household soils, it is desirable to develop an artificial or simulated dust composition that can be utilized to test various cleaning devices on their ability to pick up and remove household dust compositions, which are necessarily significantly different from soil compositions found virtually exclusively on flooring surfaces.

SUMMARY OF THE INVENTION

The synthetic testing soil of, the present invention comprises: from about 40% to 80% of at least one particulate component, and from about 20% to 60% of at least one hair component, wherein the particle size distribution of the particulate component composition is from 1% to 10% less than 75 microns; from 10% to 30% between 75 microns and 300 microns; and from 60% to 85% greater than 300 microns. In addition, an additional fiber component may optionally be present, in an amount up to about 40%. It is preferred to have the fiber component present in an amount of from about 10% to 30% by weight and most preferably from about 20% to 30% by weight. The component percentages are weight percentages based upon the total weight of the testing soil.

The testing method comprises applying a pre-measured quantity of a test soil to a specific size test surface by first, randomly but evenly distributing a particulate component of a test soil to the surface, and second, randomly but evenly distributing a hair component of a test soil to the surface by separating the hair fibers from each other into at least ten divisions of fibers and distributing these divisions of fibers to the surface; applying the cleaning product to the test surface to remove the test soil; and measuring the amount of test soil that has been removed by the cleaning product from the surface to obtain the relative efficiency of the cleaning product.

It was unexpectedly found that one synthetic soil closely mimics the soils from seven geographically diverse areas of the country, and that dry soil samples obtained from the diverse areas were less diverse in content than anticipated. Further, the specific nature of the contents of the soil were unexpected, and in particular, the particle size distribution of the materials in the particulate component of the soils was unexpected.

In addition, a simulated household dust composition of the present invention comprises a fibrous fraction present in an amount of about 45% to about 55% by weight of the composition, and a particulate fraction present in an amount of between 45% to 55% by weight of the composition in which approximately 78% to 100% by weight of the fibrous fraction is formed from cotton fibers, and in which approximately 40% to 70% by weight of the particulate fraction is formed from skin cells. As a result of additional testing, it has been unexpectedly found that a simulated household dust composition including these fractions and components of the fractions closely mimics household dust compositions found in different locations throughout the United States, which unexpectedly illustrated that very high amounts of both cotton fibers and skin cells were the majority components in these dust compositions.

These, and other aspects of the present invention will be better appreciated and understood when considered in conjunction with the following description and the accompanying examples and tables. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

DETAILED DESCRIPTION OF THE INVENTION

The present invention and the various features and advantageous details thereof are explained more fully with reference to the non-limiting embodiments described in detail in the following description.

The synthetic testing soil of the present invention was arrived at after extensive research into what constitutes a typical soil to be found in a normal home environment in the continental United States. Since it was desired to establish a soil composition which would be considered to be typical of, or representative of, any region of the country, it was determined that dirt from a variety of locations should be collected and analyzed to determine the characteristics thereof. Accordingly, seven cities across the United States were selected as geographical centers for sampling of soil or dirt from uncarpeted areas. A minimum of ten homes in each city was sampled, using a standardized vacuum cleaning sampling technique. Samples were then returned, and submitted to an independent contract test laboratory for evaluation of the physical properties of the collected dirt. From this data, variability of the physical compositions of the samples was determined. Further, data was collected at the sampling sites to indicate variations in the environment, such as whether there were pets and/or children in the household. For purposes of the present disclosure, the term "dust" is to be taken to refer to particulate materials which are airborne, and which will fall out of the air to settle on floors, tops of tables, and shelves, etc. Thus, dust is but one part of the artificial test soil developed in the present invention.

The test sites for the sampling were chosen to be Phoenix, Miami, Metropolitan New York (Newark), Kansas City, Columbus, Denver, and San Diego. Twelve homes in each of the cities were prescreened so to each have a minimum of 3 rooms which were not carpeted; including a kitchen, a bathroom, and one other room, excluding basements and laundry areas; resident(s) willing to not clean the floors in those rooms for two weeks prior to the sampling; and agreeing to permit representatives of the sampling organization into their homes to collect soil. The households were also prescreened and equally distributed between the cities on the basis of the presence of children under 18, and the presence of predominantly indoor cats and dogs. In home visits were conducted until a minimum of 10 homes had been sampled in each city. Study demographics were also weighted, based upon government statistics from 1990 and 1998, so that homes without pets constituted 40% of the sampling; homes with cats and/or dogs constituted 60% of the sampling; homes with no children under age of 18 constituted 60% of the sampling; homes with children under age of 18 constituted 40% of the sampling; urban area homes comprised 75% of the sampling; and rural area homes comprised 25% of the sampling.

Two samples were taken in each home, one from the kitchen and one from another room, resulting in a total of 20 samples from each city. In Kansas City, all samples were kept separate, and not pooled. In the remaining 6 cities, the samples were handled as follows: Kitchen samples from 3 homes were kept separate; Other room samples from 3 homes were kept separate; All kitchen samples from the remaining 7 homes were pooled (after weighing individually); All other room samples from the remaining 7 homes were pooled (after weighing individually). A total of 68 samples were thus provided for analysis.

Sampling was conducted using Hoover C2024 Port-a-Power commercial vacuum with hose and standard hard floor cleaning tool. Pre-weighed soil collection bags were removed from the vacuum cleaner immediately after sample collection from a given room, sealed, and placed in a Ziploc®, plastic bag for return to the research facility to determine gram/square foot collected per sample, and pooling as indicated above. The soil collection bags were high efficiency vacuum bags obtained from John Hopkins, made at Midwest Filtration Forms from DuPont Hysurf filtration material. The material is 95-97% polyethylene thermally bonded, and is 98.8% efficient at a 1 micron particle size at a flow rate of 30 cubic feet per minute.

After sampling, the samples were then forwarded to the independent test laboratory for analysis. Tests conducted include optical microscopy and visual exam, with chemical analysis following physical analysis to subdivide categories and to support weight estimates. Samples were categorized as comprising: Hair (animal and human); Other fibers (cotton, synthetic, or cellulose); Minerals (clay, quartz, $SiO_2$, or building materials including gypsum); Exfoliated skin; Food; Plant material (wood, leaves, paper, or insect material). Total analyses of the samples were conducted, and from the resulting information, the artificial soil of the present invention was formulated so as to correspond closely thereto.

It was found that the typical home dirt generally constitutes three components. Of these components, particulates and hair are critical for effectively replicating real world home soil. The third component is a fiber component which is a preferred but optional component. To fabricate a suitable artificial test soil, it was necessary to select specific readily available and commonly found forms or examples of each of the materials present in each of the components of the typical home dirt.

The first component of a typical dirt constitutes particulate materials. These particulate materials include a wide range of, mineral materials (such as sand, feldspar, talc, and clay), plant materials (such as dried grass and dried leaves), and food materials (such as chips or crackers, cereals, starches, proteins, etc.). The particulate component itself thus falls into three categories or types: mineral, plant, and starch/food. While it is preferred to have all three categories or types of particulate represented in the particulate mixture used to make up the test soil, suitable test soils can be formed from only one or two, of these types of particulate. If all three categories of particulate are present in the test soil, the particulate fraction preferably comprises 10% to 40% minerals, 20% to 50% food, and 5% to 40% plant material, based upon the particulate weight. The preferred ranges are: 20% to 30% minerals, 30% to 40% food debris, and 10% to 30% plant material, based upon particulate weight. If only two components are present, the particulate fraction is preferably comprised of like amounts of the two components.

A typical mineral fraction might include sand of greater than 300 microns, sand of less than 75 microns, feldspar of greater than 300 microns, feldspar of less than 75 microns, talc and clay. It is also possible to include sand and feldspar of a particle size between 75 and 300 microns. However, since the food components tend to be largely made up of particles within this range, it is not always necessary to have the sand and feldspar present in all three particle size ranges.

The sand used for the artificial test soil is common silica play sand that has been sieved to produce the appropriate size fractions. Any similar sand materials can be used. For the feldspar component, Zemex F-20, available from The Feldspar Corporation, may be used. Other similar feldspar materials can also be used. For the talc, commercially available baby powder was preferred. These products contain talc along with some fragrance. For the clay, H. C. Spinks Bandy Black clay may be used. Other similar clay materials can be used.

The second component of the particulate fraction is the plant material fraction. This fraction can include dried grass and leaves. Typical plant material can be chopped up grass clippings and chopped up dried leaves. The average length of the grass and leaf material is between about 1 micron and 1 mm. Any type of grass or leaves may be used so long as they are dried and ground to the above size range. Grass clippings from a double bladed mulching power mower made by Honda were used, and dried the grass overnight in an oven at 100° F. The dried grass was then stored in polyethylene reclosable bags until use. Over time the dried grass moisture content equilibrated with the ambient level of humidity. The leaves were chopped up to within the same particle range and dried and stored in a similar manner.

The third component of the particulate fraction is the starch/food fraction. These materials are representative of food crumbs that remain on a floor or counter top. Suitable representative materials include: crushed and sieved Cheerios®, available from General Mills; oats for oatmeal, such as Quaker Oats® old fashioned; crushed saltine crackers; and crushed dried soup mix such as Lipton® Chicken Noodle Cup-a-Soup® mix. The crushed, arid, sieved materials are blended together in appropriate amounts to maintain the desired size distribution. The starch/food component tends to have particle sizes in the 75 to 300 micron range, and also in the above 300 micron range.

The particulate component should be present in, an amount of from about 40% to 80% by weight, preferably in an amount of from about 40% to 70% by weight, and most preferably from about 50% to 65% by weight.

The second required component of the test soil is the hair component. This represents both human and pet hair commonly found in homes. The hair fraction typically can contain human, cat, and dog hair, in the following relative amounts: 30% to 40% human hair, 30% to 40% cat hair, and 30% to 40% dog hair. There are a wide variety of sources for test hair. Typical human hair is cut in 0.25 to 1 inch lengths. It is important that the hairs be fully separated from each other as they are applied to the test surface. It is also important that the hair strands be on the surface as separate strands as much as possible, and not as clumps of hair. To that end, the hair samples are divided apart on application as much as possible. It was found that a minimum of ten divisions of the hair sample is adequate, but fifteen divisions or more is preferred. One reason hair is an important component is that the oily and electrostatic nature of hair is difficult to replicate with any other material. Moreover, hair is an important component of household soil, showing how the test products react in the presence of hair is desirable.

The hair component of the soil should be present in an amount of from about 20% to 40% by weight, preferably from 20% to 30% by weight and most preferably from about 20% to 25% by weight.

In addition to the required particulate and hair fractions, it is preferred that the test soil also have some percentage of a non-hair fibrous material. Typical fibrous materials include cotton fibers, nylon fibers, polyester fibers and other natural and synthetic fiber materials such as wool, rayon, acrylics, etc. As a source of cotton, common cotton balls are useful. The cotton is separated to form short strands of fiber that resemble dust fibers. The typical length is from 5 to 25 mm. The typical nylon used is a 3 denier nylon cut into 6.35 mm lengths. A source of this material is Mini Fibers, Inc. The polyester material used is also 3 denier and cut to a length of 6.35 mm. The relative ratio of these fiber components within the fiber fraction is from 40 to 60% of natural fibers and 40 to 60% of synthetic fibers. The preferred ranges are 45% to 55% natural fibers and 45% to 55% of synthetic fibers. It is most preferred to use a blend of synthetic fibers such as a blend of nylon and polyester fibers. While it is preferred to use a 50/50 ratio of these fibers, any ratio of these fibers can be used.

If present, the fiber component should be present in an amount up to about 40%. It is preferred to have the fiber component present in an amount of from about 10% to 30% by weight and most preferably from about 20% to 30% by weight.

The test soil can be prepared by combining the two, or preferably three, components shortly before the test is conducted, or these components can be separately applied to the test surface. It is important that the components not be stored in an amount greater than to be used for a single test. This is because the components easily separate from each other and taking a small portion of the test soil from a larger store of mixture will lead to uneven results. When the components are stored in a combined fashion, they tend to agglomerate, and cannot be sampled and applied in a reproducible fashion and are of limited use in replicating real world household soil.

The test soil may also include certain optional components to reflect even more accurately real world household soils. Two of these optional materials include pollen, such as ragweed pollen, and human skin cells. Ragweed pollen is available from Air Filter Testing laboratories. Other similar pollen materials can be used. The human skin cells used were powdered human stratum corneum from Prof. Howard Mailbach. Other sources can also be used. Other optional materials can be some oils such as sebum and the like, which can be absorbed or adsorbed on to the test soil components. It is important that the oil not completely cover or occlude the particles, however. Also, some moisture can be added. For testing of dry soils, minimal added moisture is preferred. It should be recognized that the test soil components can be, and are preferably, stored so that they equilibrate moisture with the ambient conditions. For certain tests of "dried on soil", the soil can be made up as a paste with water and then applied to the surface and allowed to dry.

Testing is conducted on a clean test surface. Typical surfaces include uncarpeted vinyl flooring, ceramic tile flooring, with grout between the tiles, hardwood flooring, laminate countertop material, and the like. The soil is then scattered on the test surface in a random but relatively uniform fashion. The term "random but relatively uniform" means that there is no particular pattern to the application but there are also no discernibly larger deposits of material on limited areas of the surface. As noted above, the particulate fraction can be applied first, followed by the fiber fraction and then the hair fraction. These fractions may be applied in any particular order so long as they are applied in a random but relatively uniform fashion. With regard to the hair and fiber fractions, as noted above, it is important that these be applied to minimize the appearance of discernible clumps of hair or fiber on the floor. It is acceptable that there can be some small agglomeration of these fibers, as this replicates small dust clumps that can naturally appear on the surface to be cleaned.

The total amount of soil to be applied depends of the type of testing being done. It is important that enough soil be applied so that significant differences can be observed between testing samples. It has been found that amounts of from 0.1 to 10 grams of test soil per square meter of surface are suitable and preferred.

The surface is then cleaned by the test implement or composition. This test method is suitable for evaluating dust mitts, dusting cloths (both woven and non-woven), mops, brooms, vacuums and similar devices. The cloth materials can be natural or synthetic and may be treated or untreated with cleaning compositions, including tack materials. The cloths can also be provided with a material that provides a charge as the cloth is passed over the surface or the cloth may be pre-charged to provide an electrostatic charge.

Specific embodiments of the present invention will now be further described by the following, non-limiting examples which will serve to illustrate various features of significance. The examples are intended merely to facilitate an understanding of ways in which the present invention may be practiced and to further enable those of skill in the art to practice the present invention. Accordingly, the examples should not be construed as limiting the scope of the present invention.

EXAMPLES

A test soil, having the composition as set forth in Table 1, was prepared, and used to test a dusting cloth. Three different test surfaces were used with a minimum of twenty-five square feet of surface area: Seamless vinyl flooring, grouted 12 inch ceramic tile, and oak wood flooring. Each floor was cleaned by the following procedure: the surface was swept to remove any dirt or particulate, and a 10% isopropyl alcohol solution was applied with a trigger spray bottle, and the surface was cleaned and dried with a non-linting cloth. A 3 foot by 3 foot template was placed over the center of the floor material. A 1 gram total weight sample of the above test soil was applied to this area by sprinkling the particulate and other optional components over the floor within the template, then applying the hair component, being careful to separate the hair strands from each other using ten divisions of the hair samples, and lastly applying the fiber component in a manner to the hair component. The template was removed, and a pre-weighed dusting cloth was moved over the treated area in a continuous motion, extending out into the non-treated area, until the entire surface was treated one time. The pickup on the cloth was measured by weight and compared to the amount put down on the surface.

TABLE 1

| Soil Composition | | |
|---|---|---|
| | Percent | MATERIAL USED |
| MINERAL COMPONENT | | |
| Sand >,300 microns | 9.620 | Silica Play Sand |
| Sand <75 microns | 1.200 | Silica Play Sand |
| Feldspar >300 microns | 9.620 | Zemex F-20 |
| Feldspar <75 microns | 0.925 | Zemex F-20 |
| Talc >75 microns | 0.462 | Johnson & Johnson Baby Powder |
| Bandy Black Clay | 0.879 | H. C. Spinks |
| Subtotal | 22.706 | |
| STARCH/FOOD MATERIAL | | |
| Cheerios >300 microns | 4.700 | Crushed and Sieved |
| Cheerios 75-300 microns | 2.300 | Crushed and Sieved |
| Quaker Oats | 3.760 | |
| Lipton Cup-a-Soup | 4.700 | Chicken Noodle, Crushed not Sieved |
| Crackers | 7.530 | Crushed, not Sieved |
| | 22.990 | |
| PLANT COMPONENT | | |
| Dried crushed grass | 2.800 | Chopped grass clippings |
| Dried crushed leaves | 4.200 | Dried and chopped Maple Leaves |
| Subtotal | 7.000 | |
| TOTAL PARTICULATES | 52.696 | |
| HAIR COMPONENTS | Percent | SOURCE |
| Human Hair (0.25-1 inch) | 6.750 | Demeo Brothers, Virgin Brown Hair |
| Dog Hair | 6.750 | Biopol Laboratory |
| Cat Hair | 6.750 | Biopol Laboratory |
| Subtotal | 20.250 | |

TABLE 1-continued

Soil Composition

| OPTIONAL FIBER MATERIALS | Percent | MATERIAL USED |
|---|---|---|
| Cotton Fibers | 12.900 | Johnson & Johnson Cotton Ball fiber |
| Nylon Fibers | 6.450 | Mini Fibers, Inc., 3 denier, 0.250 inch |
| Polyester Fibers | 6.450 | Mini Fibers, Inc., 3 denier, 0.025 inch |
| Subtotal | 25.800 | |
| OTHER OPTIONAL MATERIALS | Percent | SOURCE |
| Ragweed Pollen | 0.370 | Air Filter Testing Labs |
| Human Skin Cells | 0.925 | Powdered Human Stratus Corneum |
| Subtotal | 1.295 | |
| | 100.000 | |

In this manner, it was possible to compare a number of differing cloths for effectiveness in removal of the artificial test soil. By comparison of the percentages of soil picked up by the cloths, accurate assessments of the efficacy of cleaning by each of the cloths was possible, with the numerical ratings confirming visual evaluations made at the time of testing.

Nonetheless, dust, while being generally similar in composition to soil, does have a different composition than normal household soil. For example, dust collects at locations that are normally spaced above the ground on which soil collects. Because dust collects in elevated locations, as well as on floors, dust is a necessary component of soil as described and defined previously, but due the nature of dust to be airborne, the types and particle sizes of the components of dust are somewhat different than those of soil in order for the particulate and fibrous materials forming the dust to collect in these elevated locations. Previous studies have been conducted to determine the deposition rate of household dust in elevated locations in order to figure out the rate of cleaning, or amount of dust that needs to be removed at specified intervals in order to design cleaning implements capable of picking up these amounts of dust.

However, these studies, while briefly commenting on the types of materials found in these household dust compositions, did not focus on the specific types and amounts of the components of these household dust compositions. Thus, pursuant to a study conducted by the applicant using samples of household dust obtained from five geographically distinct U.S. cities, these household dust samples were analyzed to determine the components of each of the household dust samples and the relative amounts of each of these components within the samples. What was unexpectedly and surprisingly determined was that the samples contained an inordinate amount of certain specific components, namely, skin cell and cotton fiber components, which rendered the dust composition significantly different from a normal soil composition. The reasons for the disparity in the composition between the household dust sample and a soil sample are not known, but it is assumed that one of the reasons for the difference in composition is the different sources and sizes of the fibers and particles which make up the respective soil and dust compositions, namely, the particles that are supplied from outdoor or exterior of the home sources, and sources which are due to everyday living occurrences happening within the home.

With regard to the dust samples that were obtained and analyzed, an average of the samples was taken in order to arrive at the simulated or artificial household dust composition represented below in Table 2:

TABLE 2

Dust Components by % Volume

| Measured Property | Measured Volume % | Target Volume % |
|---|---|---|
| Fibrous Fraction | | |
| Cotton Fibers | 70-100% | 83% |
| Synthetic Fibers | 10-40% | 9% |
| Hair | 1-10% | 8% |
| Particulate Fraction | | |
| Skin Cells | 40-70% | 62% |
| Construction Material and Soil | 10-40% | 12% |
| Plant Fragments | 10-40% | 16% |
| Starch | 1-10% | 4% |
| Low Temperature Combustion | 1-10% | 1% |
| Cotton | 1-10% | <1% |
| Sugar | <1% | <1% |
| Hair | <1% | <1% |
| Rust | <1% | <1% |
| Paint | <1% | <1% |
| Fungal | <1% | <1% |
| Synthetic fibers | <1% | <1% |

The composition of the simulated household dust includes a fibrous fraction in which the majority component is the cotton fibers, and a particulate fraction in which the majority component is skin cells. In addition, the particulate size of the simulated household dust sample is necessarily less than that of a soil composition due to the fact that the dust composition can be moved by airflows through a home to elevated locations on which the dust composition can collect. Thus, in the simulated dust composition, the particulate size breakdown for the various components of the simulated dust composition is represented in Table 3:

TABLE 3

Particulate Size Distribution

| Particulate Size | Number % | Number % |
|---|---|---|
| >50 microns | 1% | 0.4% |
| 10-50 microns | 18% | 19% |
| 2.5-10 microns | 40% | 37% |
| 0.3-2.5 microns | 41% | 44% |

The particular formulation of the simulated dust composition can take various forms. For example, the components for each of the fibrous fraction and particulate fraction other than the cotton fibers and the skin cells may be selected from other suitable materials and constrained only by their relative amounts as defined by the percentages disclosed in Table 2. In a preferred embodiment, the dust composition is formed with a weight fraction of each of the fibrous fraction and the particulate fraction, as well as the weight fraction of each of the various components of each of the fibrous fraction and particulate fraction as illustrated in Table 4.

TABLE 4

Dust Component Weight Fraction and Preferred Substance Constituting Component

| Component | Wt. Fraction | Preferred Component |
|---|---|---|
| Fibrous Fraction | 0.52 | |
| Cotton linters | 0.4816 | Cotton linters |
| Synthetic fibers/nylon | 0.0061 | Claremont Flock Corporation; RC352 semi dull nylon |
| Synthetic fibers/rayon | 0.0056 | Claremont Flock Corporation: NI353 semi dull rayon |
| Hair | 0.0264 | Cat Hair lot#99-0550RM Biopol Laboratory Inc. (cut to <1 mm length) |
| Particulate Fraction | 0.48 | |
| Human Skin Cells | 0.3225 | Obtained by vacuuming employees' bedding/sieved to <53 microns. Contains come small fibers, mostly cotton. |
| Plant Fragments | 0.0667 | Grass clippings, dried, chopped in a coffee grinder, sieved to <53 microns (USA standard #270). |
| Construction Debris | 0.0663 | USG Sheetrock 210: sieved <53 microns |
| Soil | 0.0061 | H. C. Spinks Bandy Black Clay (sieved <53 microns) |
| Starch | 0.0130 | Corn Starch (SCJ SOF 35293) |
| Combustion Particles | 0.0056 | Cabot Corp.: Black Pearls Carbon Black |

In addition, Table 4 illustrates the preferred substance utilized for each of the components of both the fibrous fraction and the particulate fraction. However, in addition to this preferred embodiment, other weight fractions and compositions for the simulated household dust composition are contemplated as being in the scope of this invention. More specifically, in order to alter the composition of the simulated household dust to more closely conform to a dust found in a particular location, the weight fractions of the fibrous fraction and particulate fraction, in addition to or separate from the modification of the weight fractions of the various proponents of each of the fibrous fraction and particulate fraction, can be modified in order to vary the composition of the simulated household dust composition to conform to the desired dust composition parameters.

To manufacture the test soil, first the components utilized to form the fibrous fraction are selected, weighed or otherwise measured to determine the proper amount to be used, and added to a first vial or other container to form the fibrous fraction. Next, the components for the particulate fraction are selected, weighed or otherwise measured to determine the proper amount to be used, and added to a second vial or other suitable container. Both containers are mixed separately until the various fractions contained in the separate containers appear to be homogeneous. The separate fractions are then intermixed with one another to form a homogeneous simulated dust composition with the selected weight and component fractions for the desired simulated dust composition.

With regards to industrial applicability, the invention provides an improved standardized soil and dust for testing of cleaning implements, compositions, and methods.

Although the best mode contemplated by the inventors of carrying out the present invention is disclosed above, practice of the present invention is not limited thereto. It will be manifest that various additions, modifications and rearrangements of the features of the present invention may be made without deviating from the spirit and scope of the underlying inventive concept.

Furthermore, all the disclosed features of each disclosed embodiment can be combined with, or substituted for, the disclosed features of every other disclosed embodiment except where such features are mutually exclusive.

It is intended that the appended claims cover all such additions, modifications and rearrangements. Expedient embodiments of the present invention are differentiated by the appended claims.

We claim:

1. A method for forming a simulated household dust composition, the method comprising the steps of:
    A) providing a first container and a second container;
    B) introducing a fibrous fraction component into the first container, the fibrous fraction component comprising up to about 45% to about 55% by weight of the simulated household dust, and wherein about 78% to about 100% by weight of the fibrous fraction component is formed from cotton fibers;
    C) mixing the fibrous fraction component in the first container;
    D) introducing a particulate fraction component into the second container, the particulate fraction component comprising from about 45% to about 55% of the simulated household dust, and wherein about 40% to about 70% by weight of the particulate fraction component is formed from skin cells;
    E) mixing the particulate fraction component in the second container; and
    F) mixing the fibrous fraction component from the first container with the particulate fraction component from the second container.

2. The method of claim 1 wherein the fibrous fraction component includes cotton fibers present in an amount of between about 70% to about 100% by volume of the fibrous fraction component.

3. The method of claim 2 wherein the fibrous fraction component includes synthetic fibers and hair fibers.

4. The method of claim 3 wherein the synthetic fibers are present in an amount of between about 10% to about 40% by volume of the fibrous fraction component and the hair fibers are present in an amount between about 1% to about 10% by volume of the fibrous fraction component.

5. The method of claim 1 wherein the particulate fraction component includes skin cells present in an amount of between about 40% to about 70% by volume of the particulate fraction component.

6. The method of claim 5 wherein the particulate fraction component includes plant fragments, construction material, soil, starch, and low temperature combustion products.

7. The method of claim 6 wherein the plant fragments are present in an amount of between about 10% to about 40% by volume of the particulate fraction component, the construction material and soil are present in an amount of between 10% to about 40% by volume of the particulate fraction component, the starch is present in an amount between about 1% to about 10% by volume of the particulate fraction component, and the low temperature combustion products are present in an amount of between about 1% to about 10% by volume of the particulate fraction component.

8. The method of claim 1 wherein the step of mixing the fibrous fraction component comprises mixing the fibrous fraction component until homogeneously mixed in the first container.

9. The method of claim 1 wherein the step of mixing the particulate fraction component comprises mixing the particulate fraction component until homogeneously mixed in the second container.

10. The method of claim 1 wherein the step of mixing the fibrous fraction component with the particulate fraction component comprises mixing the fibrous fraction component and particulate fraction component until homogeneously mixed.

11. A method for forming a simulated household dust composition for testing the efficacy of an elevated surface cleaning device, the method comprising the steps of:

A) introducing a fibrous fraction component into a container, the fibrous fraction component comprising up to about 45% to about 55% by weight of the simulated household dust, and wherein about 78% to about 100% by weight of the fibrous fraction component is formed from cotton fibers;

B) introducing a particulate fraction component into the container, the particulate fraction component comprising from about 45% to about 55% of the simulated household dust, and wherein about 40% to about 70% by weight of the particulate fraction component is formed from skin cells, and;

C) mixing the fibrous fraction component with the particulate fraction component to form the simulated household dust;

wherein the simulated household dust is configured to simulate concentrations of fibrous components and particulate components found on elevated surfaces.

* * * * *